United States Patent [19]

Blanco et al.

[11] 4,214,963

[45] Jul. 29, 1980

[54] PROCESS FOR THE PREPARATION OF SUBSTITUTED 4H-PYRAN-4-ONES

[75] Inventors: Jose R. Blanco, Las Arenas; Aurelio O. Venero, Lejona, both of Spain

[73] Assignee: Javier Garcia de Lama, Vecino de Bilbao, Spain

[21] Appl. No.: 963,688

[22] Filed: Nov. 27, 1978

[30] Foreign Application Priority Data

Dec. 6, 1977 [ES] Spain .................................. 464809

[51] Int. Cl.$^2$ .............................................. B01J 1/10
[52] U.S. Cl. .............................................. 204/158 R
[58] Field of Search ................................. 204/158 R

[56] References Cited

U.S. PATENT DOCUMENTS 3,973,945  8/1976  Fujino et al. ..................... 204/158 R Primary Examiner—Howard S. Williams
Attorney, Agent, or Firm—Bucknam and Archer

[57] ABSTRACT

A process for the preparation of a substituted 4H-pyran-4-one is described which consists of reacting a substituted 2,3-dihydro-4H-pyran-4-one with N-bromosuccinimide in the presence of light.

10 Claims, No Drawings

PROCESS FOR THE PREPARATION OF SUBSTITUTED 4H-PYRAN-4-ONES

There are numerous known compounds containing in their molecule the atomic group which defines the 4H-pyran-4-one, many of which are found in different plant species, often associated with a sugar.

The radicals which can be linked to the ring of the 4H-pyran-4-one are highly varied, and among the modifications are included the saturations of the double links. One relatively simple case of substitution is seen in meconic acid, with two carboxyl groups and one hydroxyl, in position 2,6 and 3 respectively. Frequent substitutions in compounds of a natural origin are the presence of a benzene ring condensed with that of the 4H-1-benzopyran-4-one. This ring is thus presented in compounds such as daidceine, where an additional condensed benzene ring tends to exist in positions 2 or 3 of the benzopyranone. In this case it is frequent for the aromatic rings to have hydroxyl or methoxyl radicals in different positions, and often some hydroxyl will link with a sugar.

Also, the 4H-pyran-4-one ring can present itself with one of the two double links saturated, by which its geometry is slightly modified on account of the lengthening of the link between the two corresponding carbon atoms. In the case of saturation of only one of the double links, we have a 2.3-dihydro-4H-pyran-4-one. Likewise, these are well-known derivatives of this ring similar to those described for the 4H-pyran-4-one which also constitute a suitable material for carrying out various syntheses leading to products of an industrial interest. Specifically, the 2.3-dihydro-2(or 3)-phenyl-4H-benzopyran-4-ones with substituents in the aromatic rings of the -OR type, where R can be a hydrogen, methyl, ethyl or even a sugar radical, are adequate compounds for the preparation of 2(or 3)-phenyl-4H-1-benzopyran-4-ones with substituents in the aromatic rings. Although, in certain cases, it is possible to have recourse to complete syntheses, these almost always turn out to be extremely laborious and with a final outcome of the process which makes it little profitable for use when preparing relatively large quantities of these compounds.

This invention is concerned with a procedure for the preparation of 4H-pyran-4-ones substituted by starting with substituted 2.3-dihydro-4H-pyran-4-ones, by means of a bromination followed by dehydrobromination, in which N-bromo succinimide is used. When any of the substituents is open to attack by the N-bromosuccinimide, it is necessary to protect it adequately, as otherwise the reaction would be complicated by a series of secondary reactions which could even prevent the obtaining of the product desired.

The reaction is effected in a solvent which is selected preferably from among the group made up by the halogenated hydrocarbons. The bromine-containing hydrocarbons have preference, although the chlorinated ones are also useful and at times are chosen, while normally iodine and fluorine containing hydrocarbons are not selected.

Generally, the reactions of this type, using N-bromo succinimide, need a catalyst, such as benzoyl peroxide or azabis-isobutyro-nitryl, which originates the free radicals, through which the process follows its course. By means of this invention, reaction conditions are had in which catalysts, such as the above, are not needed, while the reaction takes place under a radiant energy supply in the form of light. Lamps having an emission spectrum between 250 nm and 800 nm are suitable.

The following examples show some cases, in which the procedure concerned in this invention is carried out, and are given as a non-restrictive illustration.

EXAMPLE 1

In a glass beaker, equipped with a shaking device, thermometer, coolant for reflux and an adequate lighting system, place 200 liters of anhydrous tetrachloromethane and 1 Kg. of 2.3-dihydro-2-phenyl-4H-1-benzopyran-4-one. Then begin to heat, shaking well and, when the temperature reaches 50° C., add 0.8 Kg. of N-bromosuccinimide. Heating is continued until the boiling temperature of the tetrachloromethane is reached, and then this is maintained for 2 hours, after which time the reaction is considered as terminated. The solvent is distilled under low pressure and the residue is washed in water, is dried and is crystallized from petroleum ether. The product separated from the crystallization liquids is finally dried in an oven at 40° C. The dry solid melts at 97°–99° C. and shows absorption maximums at 350 and 405 nm under ultraviolet rays.

EXAMPLE 2

In a glass beaker, equipped with a shaking device, thermometer and mechanism for heating and cooling, with appropriate lighting, place 150 liters of trichloromethane free from ethanol and water. Then, after starting up the stirring device, 8 Kg. of 2.3-dihydro-5.7-dihydroxy-2-(3-hydroxy-4-methoxyphenyl)-4H-1-benzopyran-4-one 7-ramnoglucoside are added, with the hydroxyl groups protected by the formation of the corresponding acetyl derivative, and 1.5 Kg. of N-bromosuccinimide, starting up the heating device, in such a way that the temperature of the reaction mixture will progressively increase at the rate of 3° C. per minute, until reaching 60° C. Heating is kept up at this temperature for 2 hours, then increasing the heat supply in such a way that the trichloromethane can be distilled in the least time possible, until becoming a pasty residue, at which time the system is cooled until the temperature in the beaker is approximately 30° C. The product is deacetylated by means of heating with hydroalcoholic alkali and is precipitated with an aqueous solution of 20% sulfuric acid. It is allowed to set for 48 hours and the precipitate is separated from the original liquids by filtration with a vacuum, washing it alternately with water and 96% ethanol, until colorless filtrates are obtained. The solid, which is dried in an oven at 40° C., presents absorption maximums under ultraviolet rays at 255, 268 and 345 nm., which coincide with those of the 5.7-dihydroxy-2-(3-hydroxy-4-methoxyphenyl)-4H-1-benzopyran-4-one-7-ramnoglucoside.

The invention, within the framework of its essential nature, can be put into practice in other ways differing in detail from those set out in the description as examples, and for which the same protection is invoked and is included in the spirit of the claims.

Having described the purpose of this invention, the following claims are declared as new and invented by the applicants:

1. Process for obtaining substituted 4H-pyran-4-ones, wherein a substituted 2.3-dihydro-4H-pyran-4-one reacts in a solvent with N-bromosuccinimide in the presence of light and the illumination is effected with lamps having an emission spectrum between 250 nm and 800 nm in order to form a substituted 4H-pyran-4-one.

2. Process according to claim 1 wherein the solvent used is a halogenated hydrocarbon.

3. Process according to claim 1 or 2, wherein the solvent used is trichloromethane.

4. Process according to claims 1 or 2, wherein the solvent used is tetrachloromethane.

5. Process according to claim 1, wherein the substituted 2.3-dihydro-4H-pyran-4-one is a substituted 2.3-dihydro-4H-1-benzopyran-4-one.

6. Process according to claim 1, wherein the substituted 2.3-dihydro-4H-pyran-4-one is a substituted 2.3-dihydro-2-phenyl-4H-1-benzopyran-4-one.

7. Process according to claim 1, wherein the substituted 2.3-dihydro-4H-pyran-4-one is 2.3-dihydro-5.7-dihydroxy-2-(3-hydroxy-4-methozyphenyl)-4H-1-benzopyran-4-one.

8. Process according to claim 1, wherein the substituted 2.3-dihydro-4H-pyran-4-one is the 7-ramnoglucoside of the 2.3-dihydro-5.7-dihydroxy-2-(3-hydroxy-4-methoxyphenyl)-4H-1-benzopyran-4-one.

9. Process according to claim 1, wherein the substituted 2.3-dihydro-4H-pyran-4-one containing hydroxyl groups is previously acetylated and once the reaction is terminated, it is deacetylated with hydroalcoholic alkali.

10. Process according to claim 1, wherein the reaction is carried out in a beaker by illuminating said reaction beaker.

* * * * *